United States Patent [19]

Upasani

[11] Patent Number: 5,567,830
[45] Date of Patent: Oct. 22, 1996

[54] PROCESS FOR SYNTHESIS OF ACETYLENIC CARBINOLS

[75] Inventor: Ravindra B. Upasani, Foothill Ranch, Calif.

[73] Assignee: Cocensys, Inc., Irvine, Calif.

[21] Appl. No.: 195,464

[22] Filed: Feb. 14, 1994

[51] Int. Cl.$^6$ .................................................. C07J 41/00
[52] U.S. Cl. ........................ 552/575; 552/595; 552/600
[58] Field of Search ................................ 552/515, 600, 552/592

[56] References Cited

U.S. PATENT DOCUMENTS

| | | | |
|---|---|---|---|
| 2,267,257 | 12/1941 | Ruzicka | 260/397.5 |
| 2,666,769 | 1/1954 | Colton | 260/397.4 |
| 2,691,028 | 10/1954 | Colton | 260/397.5 |
| 2,725,389 | 11/1955 | Colton | 260/397.4 |
| 2,816,910 | 12/1957 | Junkmann et al. | 260/482 |
| 2,849,462 | 8/1958 | de Ruggieri | 260/397.4 |
| 2,939,819 | 6/1960 | Barton et al. | 167/65 |
| 3,135,743 | 6/1964 | Clinton et al. | 260/239.55 |
| 3,176,013 | 3/1965 | Klimstra | 260/239.55 |
| 3,413,314 | 11/1968 | Amiard et al. | 260/343.2 |
| 3,478,067 | 11/1969 | Bertin et al. | 260/397.3 |
| 3,725,439 | 4/1973 | Patchett et al. | . |
| 4,081,537 | 3/1978 | Hofmeister et al. | 424/238 |
| 4,748,024 | 5/1988 | Leonard | 424/489 |

FOREIGN PATENT DOCUMENTS

| | | |
|---|---|---|
| 736340 | 9/1955 | United Kingdom . |

OTHER PUBLICATIONS

Bond et al., "Synthesis and Biological Inactivity of Some 4α,6–Cyclo Steroids," *J. Med. Chem.* 19:255–259 (1976).

Brandsma & Verkruijsse, "Synthesis of Acetylenes and Cumulenes by Elimination Reactions," in: Synthesis of Acetylenes, Allenes and Cumulenes: A Laboratory Manual, Elsevier Scientific Publishing Co., N.Y., pp. 115, 271–272 (1981).

Brittelli & Boswell, "New Furoxan Chemistry. 1. Synthesis of Diacylfuroxans by Reaction of Ethynyl Acetates with Nitrosyl Fluoride/Nitrosonium Tetrafluoroborate," *J. Org. Chem.* 46:312–315 (1981).

Burdett & Rao, "Synthesis of 17α–Ethynyl–7α,11β–dihydroxyestra–1,3,5 (10)–triene–3,17β–diol," *J. Chem. Soc. Perkin Trans.* I:2877–2880 (1982).

Cradock et al., "Preparation and Properties of some Silyl–and Germyl–halogenoacetylenes and of Digermylacetylene," *J. Chem. Soc. Dalton*, pp. 759–763. (1978).

Gillespie & Walker, "Phosphides and Arsenides as Metal–Halogen Exchange Reagents. Part 1. Dehalogenation of Aliphatic Dihalides," *J. Chem. Soc. Perkin Trans.* I:1689–1695 (1983).

Hu & Covey, "Synthesis of 1,10–Seco–5α–estr–1–ynes: Potential Mechanism–based Inhibitors of 3α–and 3α–Hydroxysteroid Dehydrogenases," *J. Chem. Soc. Perkin Trans.* I :417–422 (1993).

Khan, N. A., "Acetylenic Compounds: VIII Reactions of α,β–vinylic dibromides with sodium in liquid ammonia," *Pakistan J. Sci. Res.* 13:87–88 (Apr. 1961).

Midland, M. M., "Preparation of Monolithium Acetylide in Tetrahydrofuran. Reaction with Aldehydes and Ketones," *J. Org. Chem.* 40:2250–2252 (1975).

*Primary Examiner*—Rebecca Cook
*Attorney, Agent, or Firm*—Sterne, Kessler, Goldstein & Fox P.L.L.C.

[57] ABSTRACT

A method for the preparation of an acetylenic alcohol by reaction of 1,2-dibromoethylene with an alkyl, aryl an heteroaryl lithium in an inert solvent, followed by reaction with a carbonyl-containing compound to give an acetylenic alcohol is disclosed.

18 Claims, No Drawings

PROCESS FOR SYNTHESIS OF ACETYLENIC CARBINOLS

FIELD OF THE INVENTION

The invention is in the field of synthetic organic chemistry. In particular, the invention relates to a method for generating an organometallic reagent and its use to prepare acetylenic carbinols, especially, steroidal acetylenic carbinols.

BACKGROUND OF THE INVENTION

Steroidal carbinols containing an ethynyl or acetylene group are important components of a number of oral contraceptives available in the market place. The usual method to manufacture these derivatives involves reaction of acetylene gas with steroidal ketones in the presence of base. Another available method is addition of lithium acetylide to the corresponding steroidal ketones. However, one disadvantage of this reagent is that it readily disproportionates into dilithium acetylide and acetylene. This reagent may be stabilized using an amine, for example, ethylenediamine. However, the resulting complex, lithium acetylide diamine, is much less reactive than the amine-free lithium acetylide. Other disadvantages include use of gaseous acetylene, and a large excess of reagent needed for the completion of reaction.

An object of the present invention is to provide a novel method to generate an organometallic reagent and its use to synthesize acetylenic carbinols.

SUMMARY OF THE INVENTION

It is an object of this invention to provide a method for generating an organometallic reagent in situ that offers significant advantages over the conventional reagents. It is also an object of this invention to use this organometallic reagent for preparing acetylenic carbinols.

In particular, the invention relates to a method for the preparation of an acetylenic alcohol, comprising reaction of 1,2-dibromoethylene with an alkyl, aryl or heteroaryl lithium in an inert solvent, followed by reaction with a carbonyl-containing (ketone or aldehyde) compound having at least one carbonyl group to give the acetylenic alcohol.

This invention also relates to a method for the preparation of an organometallic reagent which is useful for the preparation of an acetylenic alcohol, comprising reacting 1,2-dibromoethylene with an alkyl, aryl or heteroaryl lithium in an inert solvent to give the organometallic reagent.

The methods of the present invention are a great advance in the art as the reaction conditions are mild (the reaction temperature of the organometallic reagent may be as low as −100° C.), the reaction time of the ketone with the organometallic compound is short (generally less than 15 min.), the reaction gives a high yield (90–95%), it is regioselective (the organometallic reagent selectively adds to the 3-position of pregnane-3,20-diones), it is stereoselective (it produces predominantly the 3β-ethynyl-3α-hydroxy-5β-pregnane), it is general (it can be used to prepare a wide variety of acetylenic alcohols), it is cost effective, and is environmentally safe (it may be carried out without a carcinogenic solvent).

DETAILED DESCRIPTION OF THE PREFERRED EMBODIMENTS

The invention relates to a method for the preparation of acetylenic alcohols by preparing an organometallic reagent from 1,2-dibromoethylene and an alkyl lithium, an aryl lithium or heteroaryl lithium in an inert solvent at about −75° C. to −50° C., followed by reaction with a carbonyl containing compound at −100° C. to 20° C. to give, after conventional workup, the acetylenic alcohol. When 1,2-dichloroethylene was used in place of 1,2-dibromoethylene, it was discovered that the product was the 3-chloropropargyl alcohol (see Example 7). Thus, the use of 1,2-dibromoethylene allows for the preparation of an organometallic reagent that give the non-halogenated acetylenic alcohol after reaction with the carbonyl containing compound.

Examples of carbonyl-containing compounds which may be used in the practice of the invention include those having the Formula I:

wherein R and R' are independently selected from hydrogen, alkyl, alkenyl, alkynyl, aryl, substituted aryl, heteroaryl, substituted heteroaryl, a heterocyclic ring, a substituted heterocyclic ring, or where R and R' together form a substituted or unsubstituted carbocyclic or a heterocyclic ring which may contain one or more fused carbocyclic, heterocyclic, aryl or heteroaryl rings.

The carbonyl-containing compound should not be highly hindered. For example, the organometallic reagent failed to add to the 11-position of pregnan-3,11,20-trione-3,20-diketal under both normal and harsh reaction conditions. Thus, di-tert-butyl ketone would not be expected to react.

Examples of substituents on the aryl, heteroaryl, and heterocyclic rings include dialkylamino, fluoro, chloro, fluoroalkyl, chloroalkyl, cyano, alkyl, alkenyl, alkynyl, aryl, substituted aryl, heteroaryl, alkoxy, trialkylsilyl-substituted alkoxy, aryloxy, substituted aryloxy, heteroaryloxy, a heterocyclic ring, a heterocyclicoxy ring, aralkoxy and haloalkoxy.

Typical $C_{6-14}$ aryl groups include phenyl, naphthyl, phenanthryl, anthracyl, indenyl, azulenyl, biphenyl, biphenylenyl and fluorenyl groups.

Typical aryloxy groups include any of the $C_{6-14}$ aryl groups linked by oxygen, e.g. phenoxy and 1-naphthyloxy groups.

Typical substituted aryl groups include any of the $C_{6-14}$ aryl groups substituted by one or more dialkylamino, fluoro, chloro, fluoroalkyl, chloroalkyl, cyano, alkyl, alkenyl, and alkynyl groups, e.g. 2-chlorophenyl 2,4-difluorophenyl and the like.

Typical substituted aryloxy groups include any of the $C_{6-14}$ aryloxy groups substituted by one or more dialkylamino, fluoro, chloro, fluoroalkyl, chloroalkyl, cyano, alkyl, alkenyl, and alkynyl groups, and linked by oxygen, e.g. 2-chlorophenoxy, 2,4-difluorophenoxy and the like.

Typical aryloyl groups include any of the above-mentioned aryl groups substituted by a carbonyl group which may be protected as a ketal, e.g., an ethylene ketal, a propylene ketal, or a dialkoxy ketal such as dimethoxy ketal, diethoxy ketal, dipropoxy ketal, dibutoxy ketal and the like.

Typical heteroaryl groups include thienyl, benzo[b]thienyl, naphtho[2,3-b]thienyl, thianthrenyl, furyl, pyranyl, isobenzofuranyl, chromenyl, xanthenyl, phenoxanthinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinazolinyl, cinnolinyl, pterdinyl, 5aH-carbazolyl, carbozolyl, β-carbolinyl, phenanthridinyl, acrindinyl, perimidinyl, phenanthrolinyl, phenazinyl, isothiazolyl, phenothiazinyl, isoxazolyl, furazanyl and phenoxazinyl groups. Heteroaryl groups containing acidic NH groups may be protected, for example, with a t-BOC group by reaction with the reagent BOC-ON™, available from the Aldrich Chemical Co.

Typical heteroaryloxy groups include any of the heteroaryl groups linked by oxygen, e.g. 2-furanoxy, 4-pyridoxy, 2-pyrazinoxy, purine-6-oxy and the like.

Typical heterocyclic groups include tetrahydrofuranyl, pyranyl, piperidinyl, piperizinyl, pyrrolidinyl, imidazolindinyl, imidazolinyl, indolinyl, isoindolinyl, quinuclidinyl, morpholinyl, isochromanyl, chromanyl, pyrazolidinyl, pyrazolinyl and the like. Heterocyclic groups containing acidic NH groups may be protected, for example, with a t-BOC group.

Typical heterocyclicoxy groups include any of the heterocyclic groups linked by oxygen, e.g. 4-tetrahydropyranyloxy.

Typical amino groups include $NH_2$, $NHR_5$ and $NR_5R_6$, wherein $R_5$ and $R_6$ are $C_{1-4}$ alkyl groups.

Typical halo groups include fluorine and chlorine.

Typical $C_{1-10}$ alkyl groups include methyl, ethyl, propyl, isopropyl, butyl, sec.-butyl, and tert.-butyl groups as well as side chain groups present at the C-17 position of cholestane steroids such as 6-methyl-2-heptyl and 5-ethyl-6-methyl-2-heptyl groups.

Typical $C_{2-10}$ alkenyl groups include vinyl, allyl, 1-butenyl, 2-butenyl, 3-butenyl, isobutenyl and 6-methyl-2-(3-heptenyl) groups.

Typical $C_{2-10}$ alkynyl groups include propargyl, 1-propynyl, 2-propynyl, 1-butynyl, 2-butynyl and 3-butynyl groups.

Typical aralkoxy groups include $C_{1-4}$ alkoxy groups substituted by any one of the aryl groups mentioned above.

Typical haloalkyl groups include $C_{1-4}$ alkyl groups substituted by one or more fluorine or chlorine atoms, e.g., fluoromethyl, difluoromethyl, trifluoromethyl, pentafluoroethyl, 1,1-difluoroethyl and trichloromethyl groups.

Typical alkoxy groups include any one of the $C_{1-4}$ alkyl groups mentioned above linked by oxygen to any of the 5-, 6-, 7- and/or 8- positions of the quinoline ring.

Typical haloalkoxy groups include any one of the alkoxy groups substituted by one or more fluoro, chloro, bromo or iodo groups, e.g., 2-chloroethoxy, pentafluoroethyl, 3,3,3-trichloropropoxy, 4,4,4-trichlorobutoxy and the like.

Typical trialkylsilyl-substituted alkoxy groups include any one of the $C_{1-4}$ alkoxy groups substituted by a $C_{3-6}$ trialkylsilyl group, e.g. 2-trimethylsilylethoxy, 2-triethylsilylethoxy and 2-(t-butyldimethylsilyl)ethoxy and the like.

Typical $C_2-C_6$ acyl groups include acetyl, propionyl, butanoyl and pentanoyl groups which may be protected at the ketal.

Typical $C_2-C_6$ acyl groups substituted by halogen include the abovementioned acyl groups substituted by one or more fluoro or chloro groups, e.g., trifluoroacetyl.

Typical $C_5-C_8$ carbonyl-containing carbocyclic rings include cyclopentanone, cyclohexanone, cycloheptanone, and cyclooctanone, as well as bicyclic rings such as bicyclo[2.2.2]hexanone, bicyclo[3.3.1]nonanone, bicyclo[3.3.0]octanone, bicyclo[3.2.1]octanone and the like.

Typical 5- and 6- membered carbonyl-containing heterocyclic rings containing oxygen, sulfur and nitrogen include tetrahydrofuran-3-one, tetrahydrothiophen-3-one, pyrrolidin-3-one, tetrahydropyran-3-one, tetrahydropyran-4-one, piperidin-3-one, piperidin-4-one, pentamethylene sulfide-3-one and the like.

Examples of carbonyl-containing compounds having Formula I include, but are not limited to acetone, 2-butanone, 2-pentanone, 3-pentanone, cyclohexanone, 2-hexanone, diisobutyl ketone, di-sec-butyl ketone, phenylactone, acetophenone, benzophenone, β-ionone, cyclopentanone, cycloheptanone, cyclooctanone, norcamphor, xanthone, 2,4,4-trimethyl-2-cyclohexen-1-one, thujone, menthone, 1-isoquinolinyl phenyl ketone, 1-tetralone, carvone, 4-chromanone, 1-benzosuberone, 9-fluorenone, flavone, 1,4-cyclohexadienemono-ethylene ketal, camphor, bicyclo[3.3.1]-nonane-3,7-dione, bicyclo[3.3.1]nonan-9-one, cis-bicyclo[3.3.0]octane-3,7-dione, bicyclo[3.2.1]octan-2-one, 2-benzoylpyridine, 1,4-benzodioxan-6-yl methyl ketone, benz[g]isoquinoline-5,10-dione, anthrone, anthroquinone, benzoquinone, 2-acetylpyridine, 2-acetyl-1-tetralone, 1-acetylthiophene, 2-acetyphenothiazine, 1-acetyl-4-piperidone, acetylpyrazine, 2-acetylfuran, and 3-acetylcoumarin, most of which are commercially available from the Aldrich Chemical Company, Milwaukee, Wis.

Preferred ketones are in the cyclopentano-polyhydrophenanthrene series, for example, androstanolones such as androsterones, dihydrotestosterones, androstenolones such as dehydroandrosterones, androstanediones, androstenediones, etio-cholenyl-17-aldehydes, estrone, hexahydroestrone, equilin, pregnanolones, pregnenolones, pregnanediones, pregnenediones, compounds of the suprarenal cortical hormone series, cholestanone, cholestenone, as well as analogous ketones of the sterol series or derivatives thereof such as ethers (including alkyl dialkylarylsilyl and triakylsilyl ethers), mono-enol derivatives of diketones and the like.

Especially preferred are pregnane derivatives of Formula II.

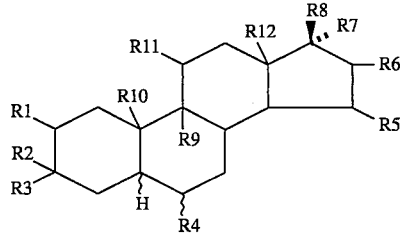

wherein R2R3 is oxo, and R1, R4, R5, R6, R7, R8, R9, R10, R11 and R12 may be alkyl, alkenyl, chloro, fluoro, cyano, hydroxy, alkoxy, dialkylamino, protected oxo or protected acyl (e.g., ethylene ketals and the like); or wherein R7R8 is oxo, and R1, R2, R3, R4, R5, R6, R9, R10, R11 and R12 may be alkyl, alkenyl, chloro, fluoro, hydroxy, alkoxy, dialkylamino, protected oxo or protected acyl;

as well as the unsaturated derivatives having 1, 2, 3, 4, or more double bonds.

An example of the acetylenic alcohols which may be prepared from the pregnane derivatives having Formula II together with the organometallic reagent of the present invention have the Formula III:

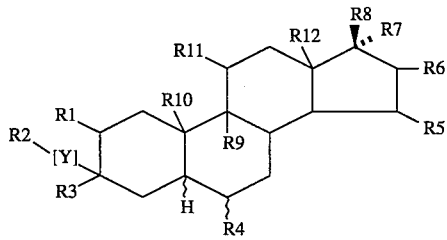

wherein Y is —C≡C—; R2 is H; R3 is OH; and R1, R4, R5, R6, R7, R8, R9, R10, R11 and R12 may be alkyl, alkenyl, chloro, fluoro, cyano, hydroxy, alkoxy, dialkylamino, protected oxo or protected acyl (e.g., ethylene ketals and the like); or an unsaturated derivative having 1, 2, 3, 4, or more double bonds.

Specific examples of carbonyl-containing steroidal compounds which may be reacted with organometallic reagent of the present invention include 3,7α,11β-trihydroxyestra-1,3,5(10)-triene-17-one (Burdett et al., *J. Chem. Soc. Perkin Trans. I* 2877–2880 (1992)), 4α,6-cyclo-5β-estra-3,17-dione 3-cyclic (ethylene acetal) (Bond et al., *J. Med. Chem.* 19:255–259 (1976)), 3-hydroxy-3a-methyl-dodecahydro-1H-benz[e]inden-7-yl acetaldehyde (Hu and Covey, *J. Chem. Soc. Perkins Trans. I*:417–422 (1993)); 3-cholestanone; testosterone; 19-nortestosterone (U.S. Pat. No. 2,849,462); estrone; estrone methyl ether; 1,4-dihydroestrone methyl ether (U.S. Pat. No. 2,691,028); pregnane-3,20-dione, pregnan-20-one, pregn-4-en-3-one, pregn-4-en-3,20-dione, 6α-methylpreg-4-en-3,20-dione, 6-methyl-3,5-dihydroxypregnan-20-one, 6-methyl-3-hydroxypregn-5-en-20-one (U.S. Pat. No. 2,939,819); 18-methyl-3,3-(2',2'-dimethyl-1',3'-propanediol)-5-and -5(10), 15-estradiene-17-one (U.S. Pat. No. 4,081,537); 4-androstene-3,17-dione (U.S. Pat. Nos. 2,384,335, 2,175,220 and 2,194,235); 3,3-(2',2'-dimethyl-1',3'-propanediol)-4-androsten-17-one; 13-ethyl-18,19-dinorpregn-4-ene-3,17-dione; 3,3-(2',2'-dimethyl-1',3'-propanediol)-13-ethyl-18,19-dinorpregn-4-en-17-one; and pregna-2,4-dien-17-one[2,3,-d]isoxazole. Preferred carbonyl-containing steroidal compounds include 5α-pregnan-3,20-dione cyclic 20-(1,2-ethanediyl acetal), 11α-dimethylamino- 5β-pregnan-3,20-dione cyclic 20-(1,2-ethanediyl acetal), 3α-hydroxy-3β-methyl-5α-androstan-17-one and 5β-pregn-11-en-3,20-dione. Where the steroidal compound has more than one carbonyl group, preferably the additional ketone groups are protected, for example, as a cyclic ketal.

Specific examples of acetylenic alcohols which can be prepared include 3β-ethynyl-3α-hydroxy-5β-pregnan-20-one, 3β-ethynyl-3α-hydroxy-5α-pregnan- 20-one, 11α-dimethylamino-3β-ethynyl-3α-hydroxy-5β-pregnan-20-one, 11α-dimethylamino-3β-ethynyl-3α-hydroxy-5α-pregnan-20-one, 3β-ethynyl- 3α-hydroxy-5β-pregn-11-en-20one, 3α,17β-dihydroxy-17α-ethynyl-5α-androstane, 3α,17β-dihydroxy-17α-ethynyl-3β-methyl-5α-androstane and 3β-ethynyl-3α-hydroxy-5β-pregn-11-en-20-one.

Examples of inert solvents which can be used in the practice of the invention include, but are not limited to ether solvents such as tetrahydrofuran (THF), diethyl ether, 1,2-dimethoxyethane, 2-methoxyethyl ether and the like. Of course, the solvent should be dried before use, for example, over molecular sieves or by distillation from lithium aluminum hydride, sodium benzophenone or calcium hydride.

Examples of alkyl, aryl and heteroaryl lithium reagents which may be used in the process of the present invention include commercially available (Aldrich Chemical Co.) methyl lithium, n-butyl lithium, sec-butyl lithium, tert.-butyl lithium, phenyl lithium and thienyl lithium. Of course, other alkyl, aryl and heteroaryl lithium reagents can be readily prepared by reaction of the corresponding alkyl, aryl or heteroaryl bromide with metallic lithium in an inert solvent such as THF or ether.

The process of this invention can be performed by reacting two equivalents of 1,2-dibromoethylene (commercially available mixture of cis- and trans-isomers) in an inert ether solvent such as THF, with about four equivalents of the alkyl or aryl lithium at a reaction temperature of about −78° C. to −60° C. under an inert atmosphere such as dry $N_2$ or argon. The reaction time for this step is normally 20–60 minutes. However, the reaction may stand at −78° C. to −60° C. for extended periods of time. The generated reagent, which is maintained at −78° C. (in a dry ice-acetone bath), is then reacted with about one equivalent of a carbonyl-containing compound in an inert ether solvent at about −78° C. Of course, where the carbonyl compound comprises an acidic proton on a hydroxy group, the group should first be protected (e.g. with t-butyldimethylsilyl chloride) or an excess of the organometallic reagent should be employed (one equivalent for each acidic proton).

The time for reaction of the organometallic reagent with the carbonyl-containing compound is about 5–30 min. The mixture is then hydrolyzed with a saturated solution of ammonium chloride or 2N HCl followed by conventional work-up (precipitation from water and/or extraction with an organic solvent and evaporation of the solvent) to afford the acetylenic carbinol.

The following examples are merely illustrative and not limitative of the remainder of the disclosure.

EXAMPLE 1

Preparation of
3β-ethynyl-3α-hydroxy-5β-pregnan-20-one

A. Preparation of the lithium reagent from 1,2-dibromoethylene

A 100 mL three-neck flask equipped with an $N_2$ gas bubbler, a thermometer, and a dropping funnel was charged with 1,2-dibromoethylene (cis/trans mixture, 98%, Aldrich, 0.164 mL, 2 mmol, mw=186, d=2.246). Dry THF (15 mL) was added and the solution was cooled to −78° C. in a dry ice-acetone bath. n-BuLi (2.5M in THF, 1,6 mL, 4 mmol) was added dropwise over a period of 10 min. The mixture was stirred at this temperature for 1 hr and the resulting reagent was used immediately for the next step.

3β-Ethynyl-3α-hydroxy-5β-pregnan-20-one

The above solution of the reagent in THF, which was maintained at −78° C., was treated dropwise with a solution of 5β-pregnan-3,20-dione cyclic 20-(1,2-ethanediyl acetal) (II, 180 mg, 0.5 mmol) in THF (15 mL). The temperature was maintained below −70° C. during the addition. The stirring was continued at the temperature for 15 min. (100% conversion as detected by TLC). The cooling bath was removed and the resulting solution was quenched with 2N HCl (pH 6). The solvent was removed and the residue was dissolved in acetone (10 mL). After adding 2N HCl (4 mL) the solution was stirred at ambient temperature for 0.5 h. The mixture was neutralized with dilute $NaHCO_3$ solution. The precipitated solid (158 mg, 93%) was collected by filtration, washed with water, and dried. The crude product was then purified by crystallization from EtOAc or from a mixture of acetone-hexane to yield the title compound; mp 196°–197° C., TLC-$R_f$ 0.45 (hexane:acetone 7.3), NMR ($CDCl_3$) δ 0.59 (s, 3H, Me), 0.97 (s, 3H, Me), 2.1 (s, 3H, Me), 2.5 (s, 1H), 2.55 (m, 1H).

EXAMPLE 2

Preparation of
3β-ethynyl-3α-hydroxy-5α-pregnan-20-one

A. Preparation of the lithium reagent from 1,2-dibromoethylene

A 250 mL three neck flask equipped with a $N_2$ gas bubbler, a thermometer, and a dropping funnel was charged with 1,2-dibromoethylene (cis/trans mixture, 98%, Aldrich, 2.1 mL, 26 mmol, mw=186, d=2.246). Dry THF (40 mL) was added and the solution was cooled to −78° C. in a dry ice-acetone bath. n-BuLi (2.5M in THF, 20 mL, 50 mmol) was added dropwise over a period of 35 min. The mixture was stirred at this temperature for 40 min. and the resulting reagent was used immediately for the next step.

B. 3β-Ethynyl-3α-hydroxy-5α-pregnan-20-one, 20 ketal

The above solution of the reagent in THF, which was maintained at −78° C., was treated dropwise with a solution of 5α-pregnan-3,20- dione cyclic 20-(1,2-ethanediyl acetal) (4.68 g, 13 mmol) in THF (50 mL) over a period of 1 hr. The temperature was maintained below −70° C. during the addition. The stirring was continued at this temperature for 15 min. (100% conversion as detected by TLC). The cooling bath was removed and the resulting solution was quenched with 2N HCl (pH 6–7). The solvent was removed and the residue was extracted with chloroform. The organic layer was separated, washed with water, and dried over anhydrous $MgSO_4$. Removal of the solvent gave an 85:15 mixture of the title product and the corresponding 3β-hydroxy epimer (combined yield 3.9 g).

EXAMPLE 3

Preparation of
11α-dimethylamino-3β-ethynyl-3α-hydroxy-5β-pregnan-20-one

Analogous to Example 1, 150 mg of 11α-dimethylamino-5β-pregnan-3,20-dione cyclic 20-(1,2-ethanediyl acetal) is reacted with the reagent prepared from 1,2-dibromoethylene and n-butyl lithium yielding 11α-dimethylamino-3β-ethynyl-3α-hydroxy- 5β-pregnan-20-one, which is purified by column chromatography over silica gel to give 40 mg of the pure title product, mp 210°–213° C.

EXAMPLE 4

Preparation of
3β-ethynyl-3α-hydroxy-5α-pregnan-20-one

Analogously to Example 2, 160 mg of 5α-pregnan-3,20-dione is reacted with the reagent prepared from 1,2-dibromoethylene and n-butyl lithium at −90° C. to −78° C. yielding 182 mg of 3β-ethynyl-3α-hydroxy- 5α-pregnan-20-one.

EXAMPLE 5

Preparation of
3α,17β-dihydroxy-17α-ethynyl-3β-methyl-5α-androstane

Analogously to Example 2, 140 mg of 3α-hydroxy-3β-methyl-5α-androstan-17-one is reacted with the reagent prepared from 1,2-dibromoethylene and n-butyl lithium at −70° C. to 10° C. yielding the title compound as white solid.

EXAMPLE 6

Preparation of
3β-ethynyl-3α-hydroxy-5β-pregn-11-en-20-one

Analogously to Example 2, 200 mg of 5β-pregn-11-en-3,20-dione is reacted with the reagent prepared from 1,2-dibromoethylene and n-butyl lithium at −95° C. to −78° C. yielding 142 mg of 3β-ethynyl-3α-hydroxy- 5β-pregn-11-en-20-one; mp 147°–150° C.

EXAMPLE 7

Preparation of
3β-chloroethynyl-3α-hydroxy-5β-pregnan-20-one

An attempt was also made to prepare the organometallic reagent with 1,2-dichloroethylene. A 100 mL three-neck flask equipped with a $N_2$ gas bubbler, a thermometer, and a dropping funnel was charged with 1,2-dichloroethylene (cis, Aldrich, 0.16 mL, 2 mmol, mw=97, d=1.28). Dry THF (7 mL) was added, and the solution was cooled to −10° C., n-BuLi (2.5M in THF, 1.6 mL, 4 mmol) was added dropwise over a period of 10 min. The mixture was stirred at −30° C. for 20 min and then at 0°–5° C. for 10 more min. The resulting reagent was then recooled to −30° C. and was treated dropwise with a solution of 5β-pregnan-3,20-dione, 20-ketal (360 mg, 1 mmol) in THF (15 mL). The cooling bath was removed and the mixture was stirred at room temp. for 30 min. (100% conversion as detected by TLC). The cooling bath was removed and the resulting solution was quenched with sat. $NH_4Cl$ solution (1 mL). The solvent was removed and the residue was dissolved in acetone (30 mL). After adding 2N HCl (5 mL) the solution was stirred at ambient temperature for 1.5 h. The mixture was neutralized with dil. NaOH solution (pH 5–6). The precipitated solid (429 mg) was collected by filtration, washed with water, and dried. The crude product was then purified by column chromatography over silica gel (toluene acetone 95:5) to yield 3β-chloroethynyl-3α-hydroxy-5β-pregnan- 20-one (130 mg); TLC-$R_f$ 0.33 (toluene:acetone 95:5), NMR ($CDCl_3$) δ 0.59 (s, 3H, Me), 0.97 (s, 3H, Me), 2.11 (s, 3H, Me), 2.55 (m, 1H).

Having now fully described this invention, it will be understood to those of ordinary skill in the art that the same can be performed within a wide and equivalent range of conditions, formulations and other parameters without affecting the scope of the invention or any embodiment thereof. All patents and publications cited herein are fully incorporated by reference herein in their entirety.

What is claimed is:

1. A method for the preparation of an acetylenic carbinol, comprising:

reacting 1,2-dibromoethylene with an alkyl, aryl or heteroaryl lithium in a dry inert solvent to give an organometallic reagent; followed by reacting said organometallic reagent with a carbonyl-containing compound whereby a carbonyl group of said carbonyl-containing compound reacts with said organometallic reagent to give the acetylenic carbinol.

2. The method of claim 1, wherein said alkyl, aryl or heteroaryl lithium is selected from the group consisting of methyl lithium, n-butyl lithium, sec-butyl lithium, tert.-butyl lithium, phenyl lithium and thienyl lithium.

3. The method of claim 1, wherein said alkyl, aryl or heteroaryl lithium is n-butyl lithium.

4. The method of claim 1, wherein said 1,2-dibromoethylene is reacted with the alkyl, aryl or heteroaryl lithium at −78° to −50° C.

5. The method of claim 1, wherein said organometallic reagent is reacted with said carbonyl-containing compound at a temperature of −100° to 20° C.

6. The method of claim 1, wherein said inert solvent is tetrahydrofuran.

7. A method for the preparation of an acetylenic carbinol, comprising:

reacting 1,2-dibromoethylene with methyl lithium, n-butyl lithium, sec-butyl lithium, tert.-butyl lithium, phenyl lithium or thienyl lithium in a dry inert solvent at −78° C. to −50° C. to give an organometallic reagent; followed by reacting said organometallic reagent with a carbonyl-containing compound at a temperature of −100° C. to 20° C. whereby a carbonyl group of said carbonyl-containing compound reacts with said organometallic reagent to give an acetylenic carbinol.

8. The method of claim 7, wherein said carbonyl-containing compound is selected from the group consisting of androstanolones, dihydrotestosterones, androstenolones, androstanediones, androstenediones, etio-cholenyl-17-aldehydes, estrone, hexahydroestrone, equilin, pregnanolones, pregnenolones, pregnanediones, pregnenediones, suprarenal cortical hormones, cholestanone and cholestenone.

9. The method of claim 7, wherein said carbonyl-containing compound is selected from the group consisting of 5α-pregnan-3,20-dione cyclic 20-(1,2-ethanediyl acetal), 11α-dimethylamino- 5β-pregnan-3,20-dione cyclic 20-(1,2-ethanediyl acetal), 3α-hydroxy-3β-methyl-5α-androstan-17-one and 5β-pregn-11-en-3,20-dione.

10. The method of claim 7, wherein said acetylenic carbinol is selected from the group consisting of 3β-ethynyl-3α-hydroxy-5β-pregnan-20-one, 3β-ethynyl-3α-hydroxy-5α-pregnan-20-one, 11α-dimethylamino-3β-ethynyl-3α-hydroxy-5β-pregnan-20-one, 11α-dimethylamino- 3β-ethynyl-3α-hydroxy-5α-pregnan-20-one, 3β-ethynyl-3α-hydroxy-5β-pregn-11-en-20-one, 3α,17β-dihydroxy-17α-ethynyl-5α-androstane, 3α,17β-dihydroxy-17α-ethynyl-3β-methyl-5α-androstane and 3β-ethynyl-3α-hydroxy-5β-pregn-11-en-20-one.

11. The method of claim 7, wherein said acetylenic carbinol is 3β-ethynyl-3α-hydroxy-5β-pregnan-20-one.

12. The method of claim 7, wherein said acetylenic carbinol is 3β-ethynyl-3α-hydroxy-5α-pregnan-20-one.

13. The method of claim 7, wherein said acetylenic carbinol is 11α-dimethylamino-3β-ethynyl-3α-hydroxy-5β-pregnan-20-one.

14. The method of claim 7, wherein said acetylenic carbinol is 11α-dimethylamino-3β-ethynyl-3α-hydroxy-5α-pregnan-20-one.

15. The method of claim 7, wherein said acetylenic carbinol is 3β-ethynyl-3α-hydroxy-5β-pregn-11-en-20-one.

16. The method of claim 7, wherein said acetylenic carbinol is 3α,17β-dihydroxy-17α-ethynyl-5α-androstane.

17. A method for the preparation of an acetylenic carbinol, comprising:

reacting an organometallic reagent with a carbonyl-containing compound at a temperature of −100° C. to 20° C. whereby a carbonyl group of said carbonyl-containing compound reacts with said organometallic reagent to give an acetylenic carbinol;

wherein said organometallic reagent is the reaction product of (a) 1,2-dibromoethylene, and (b) an alkyl, aryl or heteroaryl lithium that have been mixed together in a dry inert solvent at −78° C. to −50° C.

18. The method of claim 17, wherein said alkyl, aryl or heteroaryl lithium is selected from the group consisting of methyl lithium, n-butyl lithium, sec-butyl lithium, tert.-butyl lithium, phenyl lithium and thienyl lithium.

* * * * *